United States Patent
Koizumi et al.

(10) Patent No.: US 11,338,101 B2
(45) Date of Patent: May 24, 2022

(54) OXYGEN SUPPLY DEVICE AND METHOD FOR CONTROLLING SAME

(71) Applicant: Teijin Pharma Limited, Tokyo (JP)

(72) Inventors: Ryo Koizumi, Tokyo (JP); Sadayoshi Matsumoto, Tokyo (JP)

(73) Assignee: Teijin Pharma Limited, Tokyo (JP)

( * ) Notice: Subject to any disclaimer, the term of this patent is extended or adjusted under 35 U.S.C. 154(b) by 350 days.

(21) Appl. No.: 16/497,646

(22) PCT Filed: Mar. 19, 2018

(86) PCT No.: PCT/JP2018/010819
§ 371 (c)(1),
(2) Date: Sep. 25, 2019

(87) PCT Pub. No.: WO2018/180707
PCT Pub. Date: Oct. 4, 2018

(65) Prior Publication Data
US 2021/0283355 A1 Sep. 16, 2021

(30) Foreign Application Priority Data
Mar. 31, 2017 (JP) .............................. JP2017-071963

(51) Int. Cl.
*A61M 16/00* (2006.01)

(52) U.S. Cl.
CPC ... *A61M 16/024* (2017.08); *A61M 2202/0208* (2013.01); *A61M 2205/3334* (2013.01); *A61M 2230/205* (2013.01)

(58) Field of Classification Search
CPC ........ A61M 16/024; A61M 2202/0208; A61M 2230/205; A61M 2205/50; A61M 15/101;
(Continued)

(56) References Cited

U.S. PATENT DOCUMENTS

2006/0173257 A1 8/2006 Nagai et al.
2006/0247546 A1 11/2006 Imose
(Continued)

FOREIGN PATENT DOCUMENTS

CN 105828888 A 8/2016
JP 06-197968 A 7/1994
(Continued)

OTHER PUBLICATIONS

Office Action, dated Jun. 7, 2021, issued by the Chinese Patent Office in Chinese Application No. 201880022416.X.
(Continued)

*Primary Examiner* — Margaret M Luarca
(74) *Attorney, Agent, or Firm* — Sughrue Mion, PLLC

(57) ABSTRACT

An oxygen supply device supplying a user with an oxygen gas for inhalation acquires information of the user on percutaneous arterial oxygen saturation (SpO2) using a sensor unit, and calculates, from SpO2, the first moving average value and the second moving average value calculated over a time span longer than the first moving average in a control unit. The control unit calculates a Dip frequency during predetermined time from the SpO2 information, and when the calculated frequency is equal to or larger than the first threshold, the control unit switches the control from the control based on the first moving average value of SpO2 to the control based on the second moving average value.

6 Claims, 6 Drawing Sheets

(58) Field of Classification Search
CPC ........ A61M 16/003; A61M 2205/3306; A61M 16/10; A61M 16/022; A61M 16/00; A61B 5/14551
See application file for complete search history.

(56) References Cited

U.S. PATENT DOCUMENTS

| | | |
|---|---|---|
| 2007/0221224 A1 | 9/2007 | Pittman et al. |
| 2013/0172759 A1* | 7/2013 | Melker .................. A61B 5/20 600/476 |
| 2015/0174359 A1 | 6/2015 | Elliott et al. |
| 2016/0303405 A1 | 10/2016 | Elliott et al. |

FOREIGN PATENT DOCUMENTS

| | | |
|---|---|---|
| JP | 2007-275349 A | 10/2007 |
| JP | 2008-067941 A | 3/2008 |
| JP | 2009-530054 A | 8/2009 |
| JP | 2013-208215 A | 10/2013 |
| JP | 2014-064772 A | 4/2014 |
| WO | 2015/120521 A1 | 8/2015 |

OTHER PUBLICATIONS

Communication, dated Mar. 4, 2020, issued by the European Patent Office in European Patent Application No. EP 18 77 7562.
International Search Report of PCT/JP2018/010819 dated Jun. 26, 2018.

* cited by examiner

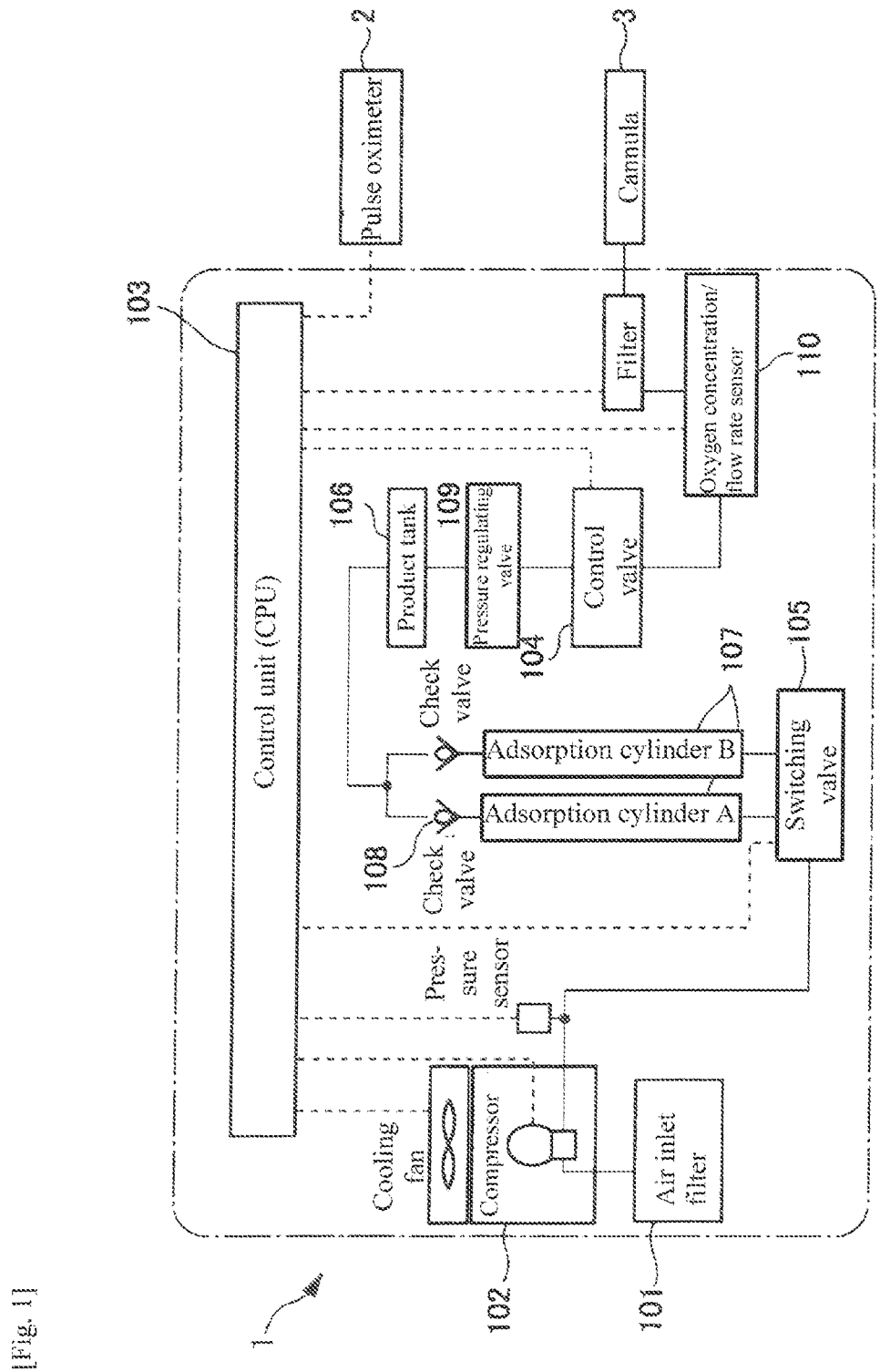
[Fig. 1]

[Fig. 2]
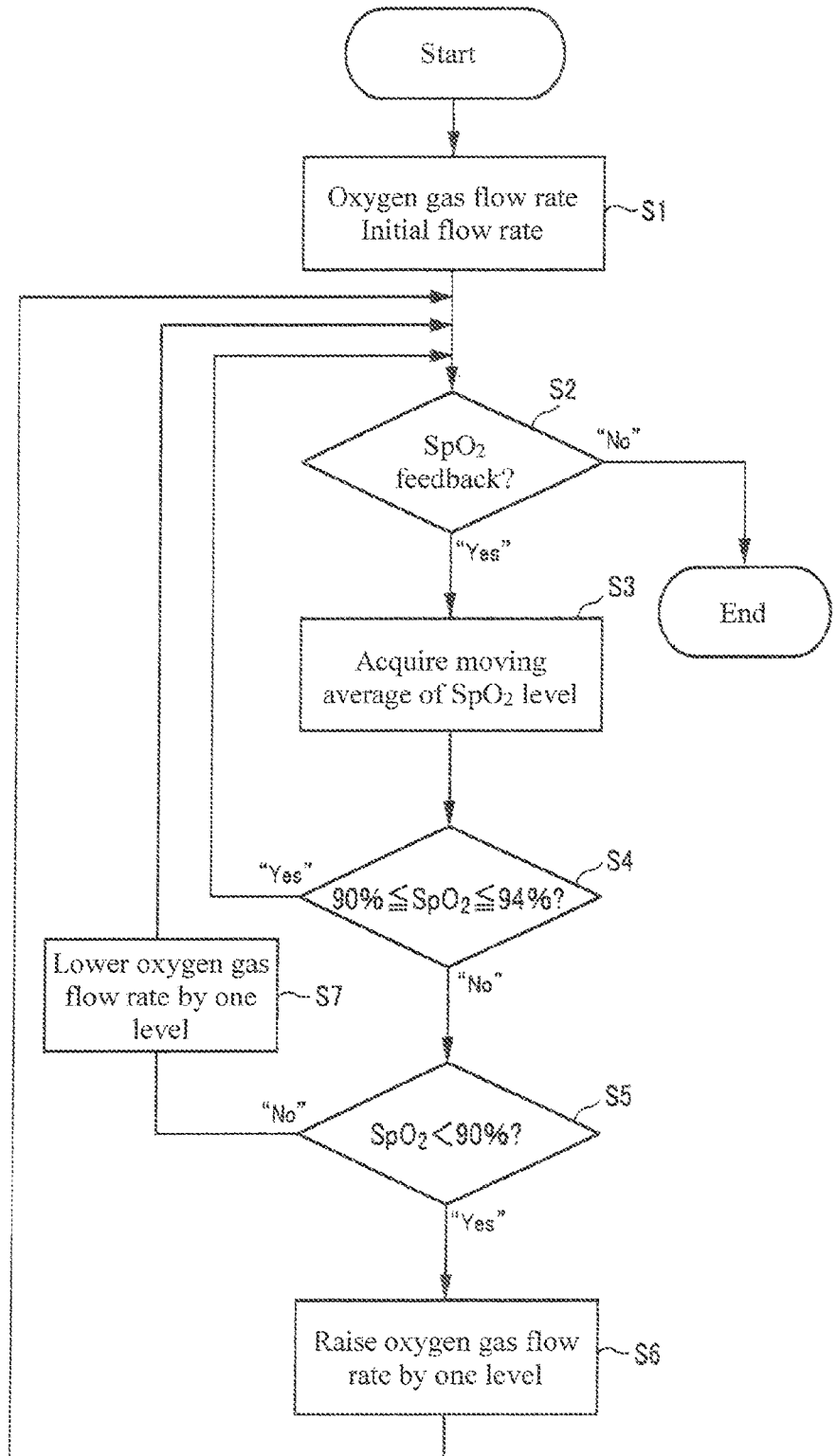

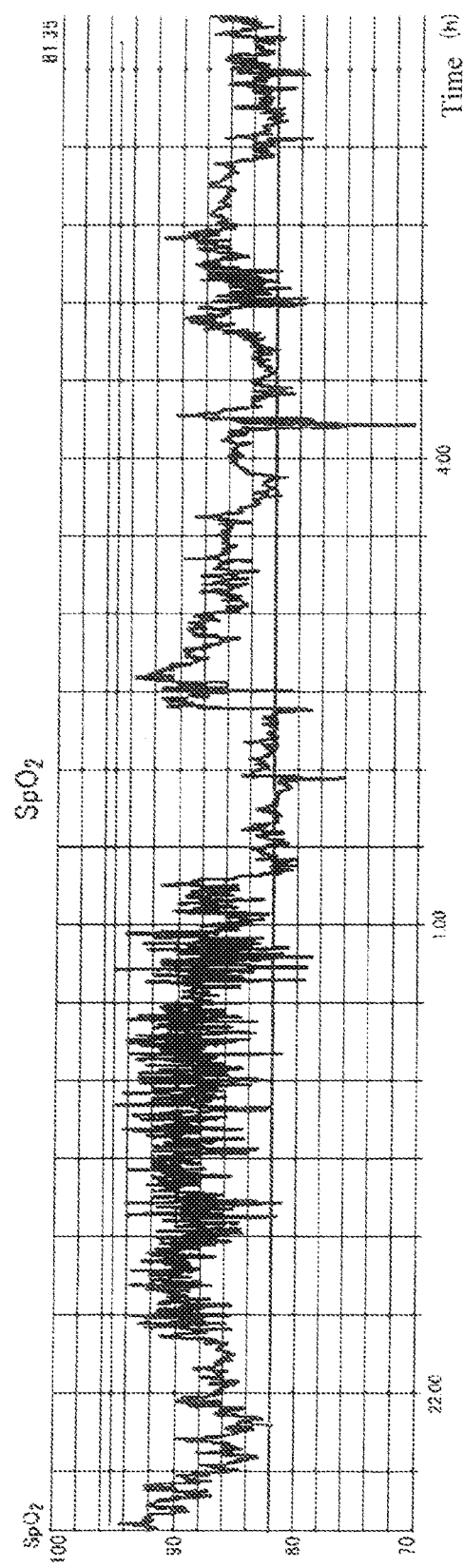

[Fig. 3B]
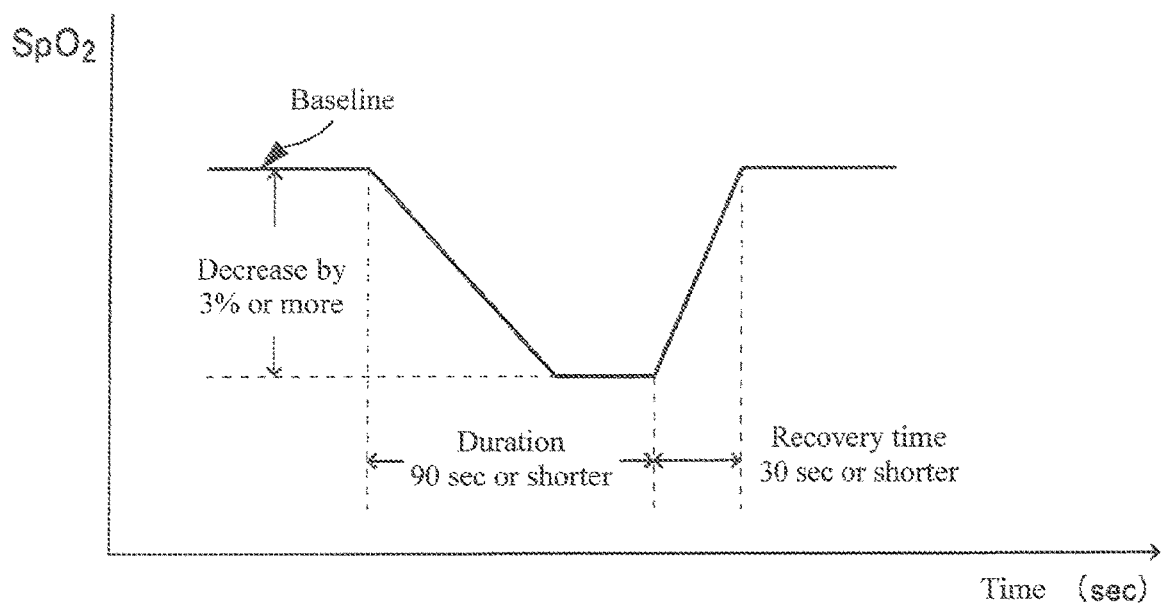

[Fig. 4]
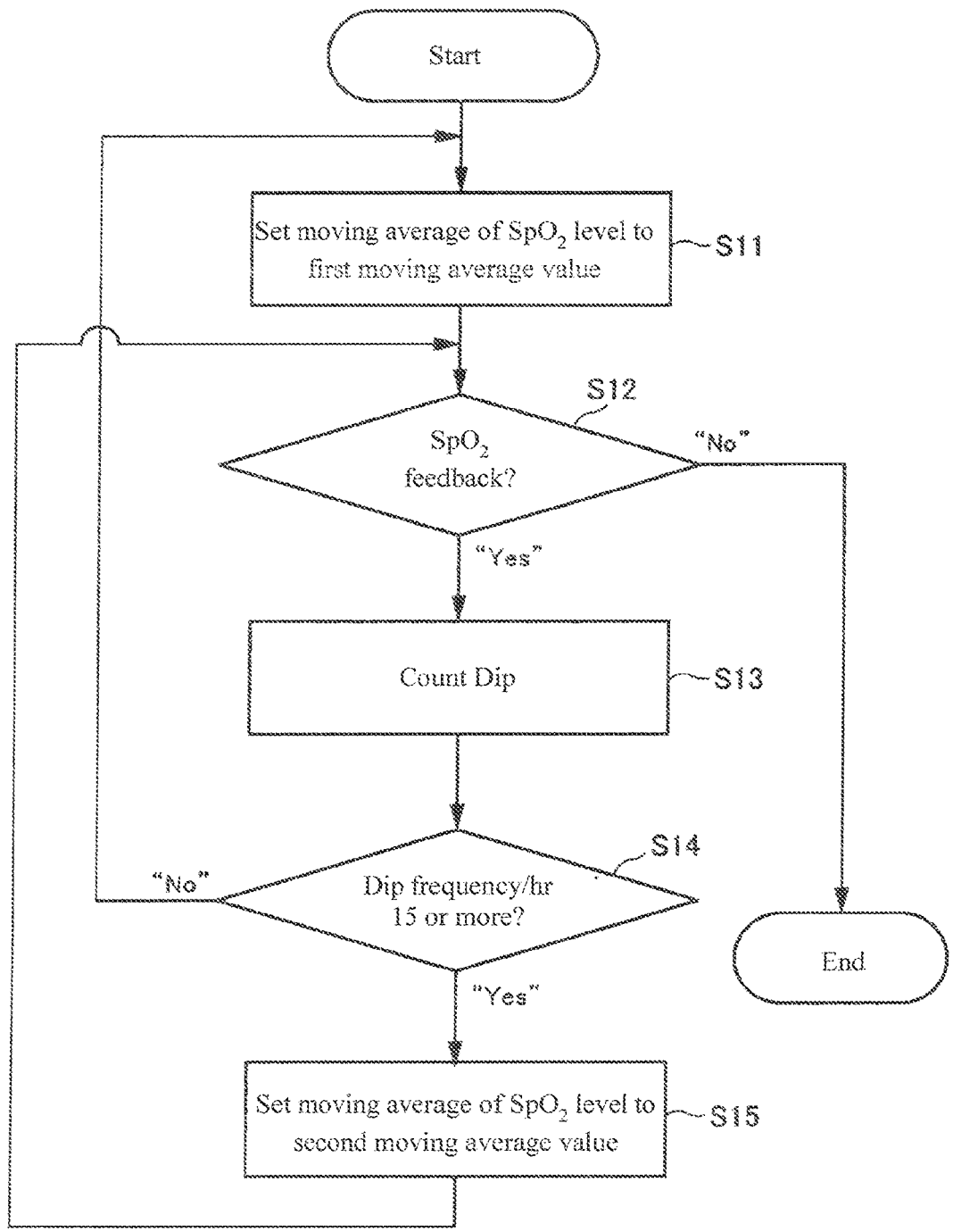

[Fig. 5A]
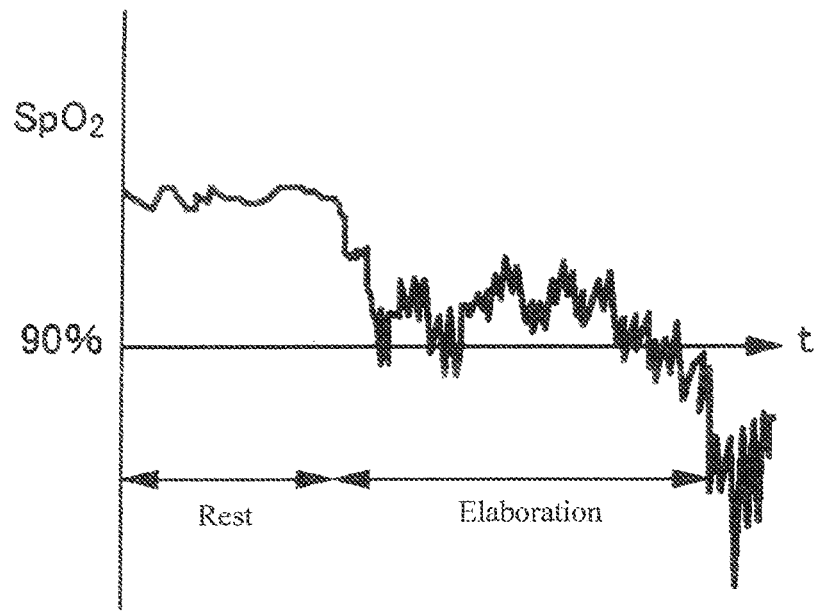
[Fig. 5B]
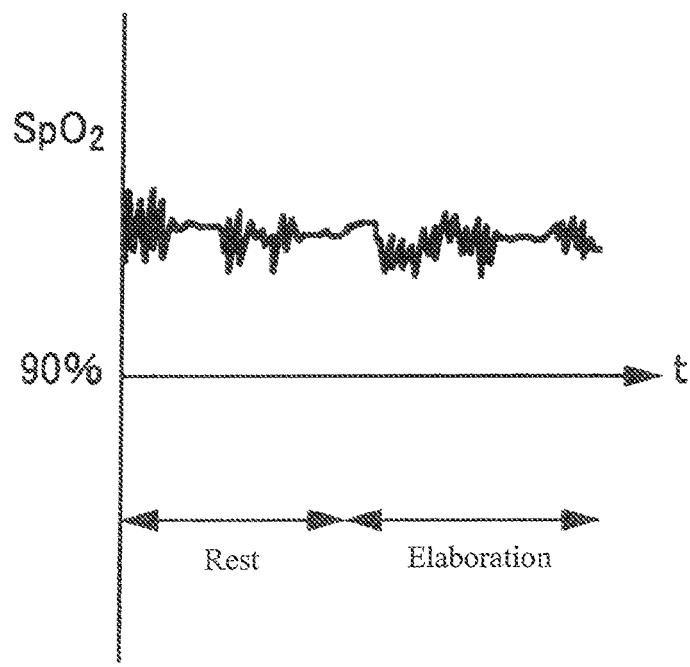

OXYGEN SUPPLY DEVICE AND METHOD FOR CONTROLLING SAME

CROSS REFERENCE TO RELATED APPLICATIONS

This application is a National Stage of International Application No. PCT/JP2018/010819 filed Mar. 19, 2018, claiming priority based on Japanese Patent Application No. 2017-071963 filed Mar. 31, 2017.

TECHNICAL FIELD

The present invention relates to an oxygen supply device used for oxygen therapy with inhalation of high concentration oxygen and a control method thereof.

BACKGROUND ART

An oxygen therapy is regarded as a therapy for chronic respiratory failure such as chronic obstructive pulmonary disease, pulmonary tuberculosis sequelae and pulmonary fibrosis and chronic respiratory disease, such as hypoxemia, caused by heart failure and other various diseases. The oxygen therapy aims to improve/prevent hypoxemia by raising oxygen partial pressure in arterial blood (PaO2) of patients through administration of high concentration oxygen gas.

A home oxygen therapy is a therapy in which a patient as a user of the oxygen supply device operates the device according to the prescription of the healthcare worker such as a physician, and receives the oxygen therapy at home. In the home oxygen therapy, the oxygen gas for inhalation is supplied from the oxygen supply device such as an oxygen concentration device and an oxygen cylinder described in PTL 1 or 2. Generally, an oxygen concentration device is used at home and a small and light-weight oxygen cylinder is often used outside home, such as going to hospital and shopping, for their convenience and ease of maintenance at use.

In the home oxygen therapy, it is desirable to prescribe the flow rate of the oxygen gas suitable for the state of each patient such as being at rest, elaboration, sleep as well as the disease and severity. For this purpose, it is under investigation to provide the oxygen supply device with a sensor measuring percutaneous arterial oxygen saturation (SpO2) as in PTL 1, and to set the flow rate of the oxygen gas based on the measured level of SpO2. Generally, it is thought to be desirable to keep a PaO2 level of a patient at 60 mmHg or more (a SpO2 level at 90% or more).

On the other hand, SpO2 is used for screening sleep apnea syndrome (SAS) patients as in PTL 3. It is known that SAS patients show appearance of a sudden downward peak (Dip) of SpO2 below baseline accompanying apnea during sleep. The number of Dip fluctuates in proportion to a degree of SAS in many cases, and thus is sometimes used at clinical site as an index for screening SAS in the form of inspection using a pulse oximeter and the like.

CITATION LIST

Patent Literature

[PTL 1] Japanese Unexamined Patent Application Publication No. H06-197968
[PTL 2] Japanese Unexamined Patent Application Publication No. 2014-64772
[PTL 3] Japanese Unexamined Patent Application Publication No. 2007-275349

SUMMARY OF INVENTION

Technical Problem

An oxygen supply device having an SpO2 feedback function is under consideration that measures SpO2 of a user, receiving a home oxygen therapy, at a predetermined interval and controls an oxygen gas flow rate so that the SpO2 is within the range of set point prescribed by a healthcare worker such as a physician and the like. Use of the SpO2 feedback function enables the oxygen concentration device to keep the SpO2 within a fixed range by controlling the flow rate of the oxygen gas supply even when oxygen consumption fluctuates depending on each state such as being at rest, elaboration and sleep and the like. In many cases, it is desirable to detect quickly the condition where SpO2 of the user is out of the range requested by a healthcare worker and accordingly change an oxygen flow rate immediately.

Use of the SpO2 feedback function enables the oxygen concentration device to control the flow rate of oxygen gas to keep the SpO2 within the prescribed range even when the user is in sleep. However, when the patient complicated with SAS receives home oxygen therapy, some control algorithm of the SpO2 feedback function may work to change an oxygen flow rate immediately responding to Dip during sleep apnea. Frequent Dip causes the SpO2 to repeat a sharp drop and a sharp rise, and thus the flow rate of the oxygen gas supply fluctuates greatly in a short time. Therefore, the user feels discomfort during sleep.

The present invention is based on the above consideration, thus aims to provide an oxygen gas supply device that can control the oxygen gas flow rate suitably for a patient regardless of the presence/absence of SAS, and a control method thereof in the oxygen supply device for home oxygen therapy having an SpO2 feedback function.

Solution to Problem

The prevalence of SAS is reported to increase with age of the subject, and among the group of patients requiring oxygen therapy, half or more are possibly complicated with SAS. The inventors of the present invention have found that there is a different physical influence caused by SpO2 decrease between the case (transient hypoxia) caused by SAS and the case (persistent hypoxia) observed in patients with respiratory illness, heart failure and the like, that the SpO2 decrease by SAS is not the original target of the oxygen therapy, and thus that the SpO2 feedback function is desired to distinguish the SpO2 decrease by SAS from the SpO2 decrease by others, and through further examination, have completed the present invention.

As a result, the present invention includes the following embodiments of (1)-(7).
(1) An oxygen supply device having a function for controlling a flow rate of an oxygen gas supplied to a user for inhalation based on percutaneous arterial oxygen saturation (SpO2) comprising: a sensor unit acquiring information on percutaneous arterial oxygen saturation (SpO2) of the user, and a control unit controlling a supply rate of the oxygen gas based on the information on percutaneous arterial oxygen saturation (SpO2) acquired from the sensor unit and calculating a moving average value of SpO2 and a Dip frequency per predetermined time from the information on percutaneous arterial oxygen saturation (SpO2), wherein the control unit calculates a first moving average value of SpO2 calculated over a first time span, a second moving average value of SpO2 calculated over a second time span which is longer than the first time span, and a Dip frequency per predetermined time from the information on percutaneous arterial oxygen saturation (SpO2) acquired by the sensor unit, selects either of the first moving average value or the second moving average value based on the calculated Dip frequency, and controls the supply rate of the oxygen gas based on the selected moving average value.

(2) The oxygen supply device according to (1), wherein the control unit controls the flow rate of the oxygen gas based on the first moving average value when the Dip frequency is less than a first threshold, and based on the second moving average value when the Dip frequency is equal to or more than the first threshold.

(3) The oxygen supply device according to (1) or (2), wherein the oxygen supply device is an oxygen concentration device that supplies an oxygen-enriched gas obtained by concentrating oxygen in the air as the oxygen gas.

(4) The oxygen supply device according to (1) or (2), wherein the oxygen supply device supplies a high-pressure oxygen gas filled in a cylinder as the oxygen gas.

(5) The oxygen supply device according to any one of (1) to (4), wherein the first time span is one second or longer and five seconds or shorter, and the second time span is two minutes or longer and five minutes or shorter.

(6) A control method for an oxygen supply device for controlling a flow rate of an oxygen gas supplied to a user for inhalation based on percutaneous arterial oxygen saturation (SpO2) comprising: a first step of acquiring information on percutaneous arterial oxygen saturation (SpO2) of the user, a second step of calculating a first moving average value of SpO2 calculated over a first time span and a second moving average value of SpO2 calculated over a second time span which is longer than the first time span from the information on percutaneous arterial oxygen saturation (SpO2), and a third step of calculating a Dip frequency per predetermined time from the information on percutaneous arterial oxygen saturation (SpO2).

(7) The control method for an oxygen supply device according to (6), further comprising a fourth step of controlling the flow rate of the oxygen gas based on the first moving average value when the Dip frequency is less than a first threshold, and based on the second moving average value when the Dip frequency is equal to or more than the first threshold.

Advantageous Effects of Invention

In accordance with the present invention, for the oxygen supply device for home oxygen therapy having an SpO2 feedback function, an oxygen gas supply device and a control method thereof can be provided that can control the oxygen gas flow rate very suitably for an SAS patient.

BRIEF DESCRIPTION OF DRAWINGS

FIG. 1 is a diagram illustrating the configuration of the oxygen concentration device of the embodiment.

FIG. 2 is a diagram illustrating the flow of the SpO2 feedback function.

FIG. 3A is a diagram illustrating the waveform of SpO2.

FIG. 3B is a diagram illustrating the waveform of SpO2.

FIG. 4 is a diagram illustrating the flow of switching between the ring average and the second moving average.

FIG. 5A is a diagram illustrating the effect by SpO2 feedback.

FIG. 5B is a diagram illustrating the effect by SpO2 feedback.

DESCRIPTION OF EMBODIMENTS

An oxygen supply device of the embodiment of the present invention is explained taking an example of an oxygen concentration device as below, however the oxygen supply device of the present invention is not limited to the oxygen concentration device. The oxygen supply device may be an oxygen supply device that supplies an oxygen gas for inhalation using a high pressure oxygen gas filled in a cylinder An oxygen supply device of the embodiment has an SpO2 feedback function for controlling a flow rate of oxygen gas supply for inhalation based on percutaneous arterial oxygen saturation (SpO2) of the user. In the case where the oxygen concentration device has a fixed flow rate for the oxygen gas supply, the users are required to operate the oxygen concentration device by themselves and change the flow rate of the oxygen gas, otherwise there may happen deficiency or excess of the oxygen gas. For example, when the user of the oxygen concentration device shifts from a rest state to an elaboration state such as standing up and then starting walking, oxygen consumption in the body increases and accordingly the SpO2 decreases as shown in FIG. 5A. Thus, unless the oxygen gas flow rate is changed from the rate prescribed for rest time to that for elaboration time, the user feels discomfort such as suffocation and the like.

On the other hand, when the SpO2 feedback function of the oxygen concentration device is activated, the oxygen gas flow rate is controlled based on the SpO2 measured with a pulse oximeter. The control unit of the oxygen concentration device detects an increase in oxygen consumption, caused by the user's shift from a rest state to an elaboration state, by a decrease in the SpO2, and then increases the oxygen gas flow rate to increase the SpO2. The increase in the oxygen gas flow rate keeps the SpO2 stable as shown in FIG. 5B, thus the user can be prevented from feeling discomfort such as suffocation and the like.

Configuration of Oxygen Concentration Device

The configuration of the oxygen concentration device of the embodiment of the present invention is represented in FIG. 1. The oxygen concentration device is a device that is used mainly in the home oxygen therapy as mentioned above and isolates nitrogen contained in the air and supplies high concentration oxygen (oxygen-enriched gas) as an oxygen gas for inhalation. The solid line and the dotted line connecting each component shown in FIG. 1 represent main gas flow path and main path of electric signal such as control signal, respectively.

The oxygen concentration device is equipped with main body 1, pulse oximeter 2 which is a sensor unit measuring SpO2 of a user of the oxygen concentration device, and cannula 3 supplying the oxygen gas to the user.

In the oxygen concentration device, main body 1 contains compressor 102 supplying compressed air, adsorption cylinders 107 filled with an adsorbent selectively adsorbing nitrogen rather than oxygen, switching valve 105 switching the sequence such as adsorption step, desorption step and the like, control valve 104 increasing or decreasing a flow rate of the concentrated oxygen gas, and the like and control unit 103 controlling these components. Control unit 103 is composed of, for example, CPU (central processing unit).

The oxygen gas is concentrated by main body 1, the flow rate of which is adjusted by control valve 104, and is supplied to a home oxygen therapy user via cannula 3. Control unit 103 controls control valve 104 so that the flow rate of the oxygen gas can be adjusted to a set point, for example, between 0.25 L/min and 5.00 L/min by an increment of 0.25 L/min. Pulse oximeter 2 as a sensor unit is attached to the fingertip and the like of the user, and measures SpO2 at a predetermined cycle (e.g., 30 Hz) and sends it to control unit 103.

The raw material air is taken into main body 1 through the air inlet provided with air inlet filter 101, which removes foreign substances such as dusts. At this time, about 21% of oxygen gas, about 77% of nitrogen gas, 0.8% of argon gas, and 1.2% of carbon dioxide and other gases are contained in the air. The oxygen concentration device concentrates the oxygen gas necessary for respiration gas and takes it out.

The raw material air taken into main body 1 is compressed by compressor 102, transferred to adsorption cylinders 107 filled with an adsorbent made of zeolite and the like which selectively adsorbs nitrogen molecules. Control unit 103, by operating switching valve 105, in turn, switches the target adsorption cylinders 107 and then supplies the compressed raw material air to the cylinder, and selectively adsorbs and removes the nitrogen gas that occupies about 77% of the raw material air in the adsorption cylinders 107.

Adsorption cylinders 107 can adopt a well-known configuration such as multiple-cylinder type of three or more cylinders as well as single-cylinder and double-cylinder types, and for the purpose of continuous and efficient manufacture of oxygen-enriched gas from the raw material air, adsorption cylinders 107 preferably adopt a double-cylinder type or a multiple-cylinder type. In the case of a pressure swing adsorption type (PSA type) oxygen concentration device of a double-cylinder type, while one adsorption cylinder (cylinder A) executes an adsorption step, the other cylinder (cylinder B) executes a desorption step, and switching valve 105 is controlled so that steps of both cylinders are switched in turn between adsorption step and desorption step each in an opposite phase, and thus oxygen-enriched gas is manufactured continuously.

As compressor 102, adopted is a compressor having only compression function or compression and vacuum functions such as a two-head swing-type air compressor, and in some cases, rotation-type air compressors including screw type, rotary type, scroll type and the like. A power supply for a motor driving compressor 102 may be AC or DC.

The nitrogen gas in the air is adsorbed on the adsorbent in adsorption cylinder 107 at pressurized state, and the oxygen-enriched gas mainly composed of the unadsorbed oxygen is taken out of adsorption cylinder 107. The oxygen-enriched gas taken out flows into product tank 106 through check valve 108 provided to prevent backflow into adsorption cylinder 107 and is accumulated in product tank 106. The oxygen-enriched gas accumulated in product tank 106 is an oxygen gas with high concentration of, for example, 95%.

Control unit 103 controls control valve 104 to adjust the oxygen gas to a flow rate prescribed by a physician and the like and supplies the oxygen gas to a patient through cannula 3. Oxygen concentration/flow rate sensor 110 feeds back values of flow rate and oxygen concentration of the supplied oxygen gas to control unit 103, and manufacture and supply of the oxygen gas by the oxygen concentration device are controlled.

SpO2 Feedback Function

An example of SpO2 feedback control executed by control unit 103 is shown in FIG. 2. When the oxygen concentration device is set to SpO2 feedback mode, control unit 103 controls control valve 104 so that the oxygen gas supplied to the user through cannula 3 is adjusted to a predetermined initial flow rate (step S1). Then, control unit 103 confirms that SpO2 feedback mode is activated (step S2), and starts the acquisition of SpO2 information using pulse oximeter 2 at a predetermined cycle.

Once the acquisition of SpO2 information is started, control unit 103 calculates a moving average value of SpO2 at each cycle and stores it in a storage unit such as memory. At least two types of moving average value are calculated for SpO2: the first moving average value of SpO2 calculated over a short span (e.g., one second or longer and five seconds or shorter), and the second moving average value of SpO2 over a longer span than the time span for the first moving average value (e.g., two minutes or longer and five minutes or shorter).

In step S3, control unit 103 acquires, at a predetermined time interval, the latest value from time series of the moving average value of SpO2 in a storage unit such as memory. The moving average value of SpO2 acquired in step S3 is either the first moving average value or the second moving average value. It is explained below which of the first moving average value and the second moving average value is acquired.

Control unit 103 checks whether the acquired moving average value of SpO2 is in the prescribed range of SpO2 (e.g., 90% or more, 94% or less) (step S4). If the moving average value of SpO2 is within the prescribed range of SpO2, control unit 103 goes back to step S2, and repeats feedback control until SpO2 feedback mode is off.

When judging that the moving average value of SpO2 is out of the prescribed range of SpO2 (e.g., less than 90% or more than 94%) in step S4, control unit 103 raises the flow rate of the oxygen gas by one level in the case of the moving average value of SpO2<90% (step S5, step S6) and increases the oxygen gas supply to the user to increase SpO2. Control unit 103 lowers the flow rate of the oxygen gas by one level in the case of the moving average value of SpO2>94% (step S5, step S7).

Control unit 103 controls control valve 104 to increase/decrease the flow rate of the oxygen gas. For example, in the oxygen concentration device of the embodiment, the flow rate of the oxygen gas can be adjusted by a division of 0.25 L/min, and thus the raising/lowering the oxygen gas flow rate by one level corresponds to an increase/decrease of the flow rate by 0.25 L/min. Control unit 103 increases/decreases the flow rate of the oxygen gas when the moving average value of SpO2 is below/over the prescribed range of SpO2, and returns SpO2 within the range of SpO2 prescribed by a healthcare worker, thus preventing the user from feeling discomfort even during sleep, which is expected to enhance the effect of the home oxygen therapy. The method for adjusting flow rate is not limited to the above-mentioned method, and a method such as, for example, PID control may be adopted.

Judgment of SAS Symptom and Switch of Moving Average Value

In the oxygen concentration device of the embodiment, the moving average value of SpO2 used for the control is switched, after judging the presence of SAS symptom, between the first moving average value and the second moving average value calculated over longer time span than the first moving average. As mentioned above, it is known that an apnea symptom of an SAS patient during sleep causes an appearance of a sudden downward peak (Dip) of SpO2 below baseline (PTL 3). The oxygen concentration device measures SpO2 of the user during sleep using pulse oximeter 2, and control unit 103 detects an appearance of Dip.

An example of waveform of SpO2 during sleep measured from an SAS patient is shown in FIG. 3A. FIG. 3A shows frequent appearances of Dip, a sudden downward peak of SpO2, during about 22:00-2:00. Control unit 103 of the oxygen concentration device, when recognizing the appearance of a peak as represented in FIG. 3B, having a decrease of 3% or more from the base line within 90 seconds and a recovery within 30 seconds, judges and counts this peak as Dip. At this time, the baseline is prepared using moving average of SpO2 calculated over, for example, 3 minutes.

Then, when a Dip frequency during predetermined time is equal to or more than the first threshold set in advance, control unit 103 judges that with high possibility, the user is an SAS patient and shows an apnea symptom. Generally, oxygen desaturation index (ODI: Dip appearance frequency per hour) of less than 15 is judged as no occurrence of an SAS symptom, and ODI of 15 or more can be judged as highly possible occurrence of an SAS symptom, and thus the first threshold may be set to, for example, 15 Dips per hour.

Control unit 103 starts measurement of SpO2 using pulse oximeter 2 at a predetermined cycle, and, at the same time, starts calculation of a moving average value of SpO2: the first moving average value and the second moving average value over a time span longer than the span for the first moving average value. The first moving average value is a moving average value calculated from SpO2 over the latest, for example, 2 seconds, and the second moving average value is a moving average value calculated from SpO2 over the latest, for example, 2 minutes.

Control unit 103 acquires the first moving average value as the moving average value of SpO2 of step S3 in FIG. 2 as an initial setting and executes SpO2 feedback control. The first moving average value is calculated from SpO2 over a time span of 2 seconds, and enables fine control of the gas flow rate. Thus, when SpO2 slightly deviates from the prescribed range of SpO2, control unit 103 immediately increases/decreases the oxygen gas flow rate, and can return the SpO2 within the prescribed level. As long as the Dip frequency during predetermined time is less than the first threshold, control unit 103 executes SpO2 feedback control using the first moving average value.

When the Dip frequency during predetermined time is equal to or more than the first threshold, control unit 103 judges that with high possibility, the user is an SAS patient and shows an apnea symptom, and switches the moving average value of SpO2 acquired in step S3 from the first moving average to the second moving average. The switch to the second moving average value calculated over the latest 2 minutes can reduce the influence from the Dip appearing in the SpO2 waveform of SAS patients. The SpO2 feedback control of FIG. 2 using the second moving average value can prevent the oxygen gas flow rate from greatly increasing/decreasing in a short time due to frequent occurrence of Dip in a short time. Thus, it can prevent a user in sleep from feeling discomfort due to a sudden change in the oxygen gas flow rate.

After the moving average value of SpO2 is switched from the first moving average value to the second moving average value, when detecting that the Dip frequency during a predetermined time is less than a second threshold, control unit 103 may switch the moving average value of SpO2 acquired in step S3 of FIG. 2 back to the first moving average value from the second moving average value. The second threshold may be the same as the first threshold, or may be smaller than the first threshold considering safety.

An example of the control flow to switch between the first moving average value and the second moving average value depending on the Dip frequency during a predetermined time is shown in FIG. 4. When the oxygen concentration device is set to an SpO2 feedback mode, control unit 103 counts the occurrence of Dip according to the flow of FIG. 4 while controlling the oxygen gas flow rate according to the flow of FIG. 2. At first, control unit 103 gives an instruction to assign the first moving average value to the moving average value of SpO2 acquired in step 3 (step S11). Then, control unit 103 confirms that the SpO2 feedback mode is activated (step S12), and then counts the Dip frequency (step S13).

Control unit 103 judges whether the counted Dip frequency per hour is equal to or more than the first threshold of 15 (step S14), and when the frequency is less than 15, returns to step S11. When the frequency is 15 or more, control unit 103 gives an instruction to assign the second moving average value to the moving average value of SpO2 to be acquired in step 3. As long as the Dip frequency per hour is equal to or more than the first threshold of 15, the moving average value of SpO2 used in control flow of FIG. 2 is the second moving average value, and the Dip occurrence can be prevented from causing a large increase/decrease of the oxygen gas flow rate in a short time.

Though the preferred embodiment of the present invention was explained in detail as above, the present invention is not limited to the embodiment mentioned above, and various kinds of variation and modification are possible within the contents of the present invention described in the scope of claims.

INDUSTRIAL APPLICABILITY

In accordance with the present invention, an oxygen gas supply device and a control method thereof can be provided that feedbacks SpO2 while switching among moving average values of SpO2 over different time spans and can control the oxygen gas flow rate suitably even for an SAS patient.

REFERENCE SIGNS LIST

1. Main body
2. Pulse oximeter
3. Cannula
101. Air inlet filter
102. Compressor
103. Control unit
104. Control valve
105. Switching valve
106. Product tank
107. Adsorption cylinder
108. Check valve
109. Pressure regulating valve
110. Oxygen concentration/flow rate sensor

The invention claimed is:

1. An oxygen supply device having a function for controlling a flow rate of an oxygen gas supplied to a user for inhalation based on percutaneous arterial oxygen saturation (SpO2), the oxygen supply device comprising:
   a sensor unit configured to acquire information on percutaneous arterial oxygen saturation (SpO2) of the user, and
   a control unit configured to control a supply rate of the oxygen gas based on the information on percutaneous arterial oxygen saturation (SpO2) acquired from the sensor unit and calculate a moving average value of SpO2 and a Dip frequency per predetermined time from the information on percutaneous arterial oxygen saturation (SpO2),
   wherein the control unit is further configured to:
   calculate a first moving average value of SpO2 calculated over a first time span, a second moving average value of SpO2 calculated over a second time span which is longer than the first time span, and a Dip frequency per predetermined time from the information on percutaneous arterial oxygen saturation (SpO2) acquired by the sensor unit,
   select either of the first moving average value or the second moving average value based on the calculated Dip frequency, and
   control the supply rate of the oxygen gas based on the selected moving average value.

2. The oxygen supply device according to claim 1, wherein the control unit is further configured to control the flow rate of the oxygen gas based on the first moving average value when the Dip frequency is less than a first threshold, and based on the second moving average value when the Dip frequency is equal to or more than the first threshold.

3. The oxygen supply device according to claim 1, wherein the oxygen supply device is an oxygen concentration device that supplies an oxygen-enriched gas obtained by concentrating oxygen in the air as the oxygen gas.

4. The oxygen supply device according to claim 1, wherein the oxygen supply device is configured to supply a high-pressure oxygen gas filled in a cylinder as the oxygen gas.

5. The oxygen supply device according to claim 1, wherein the first time span is one second or longer and five seconds or shorter, and the second time span is two minutes or longer and five minutes or shorter.

6. A control method for an oxygen supply device for controlling a flow rate of an oxygen gas supplied to a user for inhalation based on percutaneous arterial oxygen saturation (SpO2), the control method comprising:
   acquiring information on percutaneous arterial oxygen saturation (SpO2) of the user,
   calculating a first moving average value of SpO2 calculated over a first time span and a second moving average value of SpO2 calculated over a second time span which is longer than the first time span from the information on percutaneous arterial oxygen saturation (SpO2);
   calculating a Dip frequency per predetermined time from the information on percutaneous arterial oxygen saturation (SpO2); and
   controlling the flow rate of the oxygen gas based on the first moving average value when the Dip frequency is less than a first threshold, and based on the second moving average value when the Dip frequency is equal to or more than the first threshold.

* * * * *